United States Patent [19]

Miller et al.

[11] Patent Number: 5,494,935
[45] Date of Patent: Feb. 27, 1996

[54] METHODS FOR ORAL DECORPORATION OF METALS

[75] Inventors: Scott C. Miller; Friedrich W. Bruenger, both of Salt Lake City, Utah

[73] Assignee: University of Utah Research Foundation, Salt Lake City, Utah

[21] Appl. No.: 415,361

[22] Filed: Apr. 3, 1995

Related U.S. Application Data

[63] Continuation-in-part of Ser. No. 822,342, Jan. 17, 1992, Pat. No. 5,403,832.

[51] Int. Cl.[6] ............................................. A61K 31/13
[52] U.S. Cl. .................. 514/674; 514/579; 514/663; 514/673; 424/639
[58] Field of Search ...................... 424/9, 639; 514/674, 514/579, 663, 673

[56] References Cited

U.S. PATENT DOCUMENTS

| | | | |
|---|---|---|---|
| Re. 31,463 | 12/1983 | Loberg et al. | 424/1.1 |
| 2,532,392 | 12/1950 | Bersworth | 260/534 |
| 3,228,904 | 1/1966 | Morris et al. | 260/29.7 |
| 3,580,950 | 5/1971 | Bersworth | 260/534 |
| 3,650,963 | 3/1972 | Werdehausen et al. | 252/102 |
| 4,134,971 | 1/1979 | Inoue et al. | 424/128 |
| 4,141,968 | 2/1979 | Kunz et al. | 424/48 |
| 4,142,050 | 2/1979 | Kunz et al. | 544/322 |
| 4,294,853 | 10/1981 | Williams et al. | 424/319 |
| 4,352,751 | 10/1982 | Wieder et al. | 260/112 |
| 4,410,688 | 10/1983 | Denkwalter et al. | 528/328 |
| 4,585,780 | 4/1986 | Hider et al. | 514/348 |
| 4,824,986 | 4/1989 | Gansow | 558/17 |
| 4,826,673 | 5/1989 | Dean et al. | 424/9 |
| 4,831,175 | 5/1989 | Gansow et al. | 558/17 |
| 5,077,037 | 12/1991 | Wallace | 424/9 |
| 5,403,862 | 4/1995 | Miller et al. | 514/674 |

FOREIGN PATENT DOCUMENTS 866492  4/1961  United Kingdom.

*Primary Examiner*—Douglas W. Robinson
*Assistant Examiner*—James O. Wilson
*Attorney, Agent, or Firm*—Madson & Metcalf

[57] ABSTRACT

Several new powerful chelating agents, suitable for the removal of a variety of certain heavy metal ions from the body of a mammal by oral application, have been synthesized and tested. Structurally, these compounds are partially lipophilic polyaminocarboxylic acids (PACA). They were synthesized in non-aqueous media from triethylenetetramine (TT) by monoalkylation of a primary amino group, followed by exhaustive carboxymethylation of the remaining amino groups using ethylbromoacetate and subsequent alkaline hydrolysis of the ester. In contrast to their non-lipophilic counterparts EDTA and DTPA, compositions of the present inventions exhibit appreciable absorption from the intestine and, therefore, can be administered orally. By varying the length of the alkyl chain, the chelons can be directed primarily to selected target organs. In addition, the compounds can be modified to target particular absorbed heavy metals.

23 Claims, 2 Drawing Sheets

METHODS FOR ORAL DECORPORATION OF METALS

RELATED APPLICATIONS

This application is a continuation-in-part of U.S. Ser. No. 822,342, filed Jan. 17, 1992, now U.S. Pat. No. 5,403,362, issued Apr. 4, 1995, entitled "Compositions and Methods for Oral Decorporation of Metals", which patent is incorporated herein by this reference.

BACKGROUND

1. The Field of the Invention

The present invention is related to compositions which are capable of removal of certain metals from the body of animals or humans, and which compositions are capable of oral administration. More particularly, the present invention is related to partially lipophilic polyaminocarboxylic acids and methods for their use in the removal of heavy metals from specific organs in the body of a recipient.

2. Technical Background

Metal poisoning is a serious health problem. Metal poisoning can occur in several different contexts and can potentially involve a wide variety of metals. One of the most common types of metal poisoning is lead poisoning. Until recently, lead was commonly included in paints and as a gasoline additive. Accordingly, contact with lead in the urban environment or in the home was very common, and is still a major health concern. Other types of metals are also commonly encountered in the modern environment. For example, workers in metal related industries are constantly placed in environments which may contain unhealthful levels of metals. The same is true of workers in industries which deal with radioactive materials, including nuclear power, scientific research, and mining of radioactive metals.

To appreciate the potential scope of metal poisoning, it is useful to consider lead as an example. Children exposed to lead are known to suffer a number of health problems. These problems range from stomach aches and general irritability, to severe and irreversible brain damage. Children who are exposed to excessive levels of lead are commonly known to suffer from learning disabilities and a reduction in IQ.

In the United States, the primary source of lead poisoning is paint in the home. It is estimated that the walls of 57 million houses in the United States contain lead paint. As a result, the incidence of increased levels of lead in children is widespread. The Environmental Protection Agency estimates that one in nine children under the age of 6 has enough lead in his blood to be considered at risk. The United States Public Health Service places that figure as high as one child in six, and one in two in inner city neighborhoods. As a result, it is apparent that lead poisoning is a very serious health problem in the United States and the effects of the problem can be devastating, not only to the individual but to society as a whole.

Another class of metals that is of concern, and which is dealt with by the present invention, are lanthanide (4f) and actinide (5f) elements. The primary problem presented by contamination by these materials is radiation toxicity, as opposed to chemical toxicity. The increasing use of radioactive materials has introduced greater risk of poisoning by these and other radioactive metals. Indeed, a number of accidents of varying scope have occurred involving these materials. Some of the most notable accidents involving these materials have occurred in Eastern Europe and the former Soviet Union. However, smaller incidences of exposure are more common and widespread.

The effects of contamination by actinides and lanthanides is well documented in the literature. In animal studies, malignant neoplasms are known to occur over a wide range of doses. The carcinogenic potential of these elements in humans is not fully known, but cancers would be expected based upon human exposures to other alpha-emitting bone-seeking isotopes, such as radium. Thus, it will be appreciated that the contamination by radioactive elements (nuclides) is also a serious concern.

The most common treatment for metal poisoning is "chelation therapy." Conventional chelation therapy involves intravenous injection of a chelating agent into the patient. Widely known and conventional chelating agents such as EDTA. (ethylenediaminetetraacetic acid) and DTPA (diethylenetriamine pentaacetic acid) are often employed. Conventional chelation therapy is very painful to the patient and has only limited effectiveness.

The most commonly used agent for the removal of 5f elements and several other heavy metals from the body is DTPA. DTPA is usually applied either as the calcium or zinc chelate. The soluble sodium salt and the chelates formed are strongly hydrophilic. Therefore, as mentioned above, the preferred route of administration is by intravenous injection, although other forms of administration, such as inhalation, have been proposed or used in animal studies.

More recently, a new group of chelating agents, based on some naturally occurring, bacterially produced iron chelators have been developed and tested. These compounds structurally are linear catechoylamides that preferentially bind the tetravalent plutonium. Most, but not all, of these compounds are also strongly hydrophilic.

In general, strongly hydrophilic properties result in relatively rapid, primarily urinary, excretion. Thus, entry of the drug into cells, the site of the major fraction of metal deposition within the patient, is seriously limited. This property limits the overall effectiveness of the drug. Hydrophilic compounds are usually poorly absorbed from the intestine. Therefore, hydrophilic chelators require parenteral application which, in general, necessitates the presence of a physician or other certified health professional for their administration.

Parenteral application repeated over extended periods is inconvenient to the patient and sometimes difficult to maintain. The effectiveness of the treatment also diminishes rapidly with time after exposure, and the necessity of parenteral administration often increases the critical time period between exposure and first treatment. Very often, long treatment periods are required to achieve the desired reduction of the heavy metal burden.

In summary, metal poisoning and contamination is a serious health problem. Metal poisoning ranges from relatively widespread lead poisoning, to more infrequent cases of poisoning by radioactive actinides and lanthanides. In many situations, however the effect of metal poisoning can range from serious to catastrophic. The effect on the individual and the society as a whole is serious and of major concern.

As mentioned above, the most widely accepted treatment for metal poisoning or contamination is intravenous administration of a chelating agent. Most chelating agents used in this type of therapy, however, are generally hydrophilic, rapidly excreted, and have only limited ability to penetrate cells in order to remove the subject metals. Thus, the use of EDTA in the treatment of lead poisoning, for example, is effective in removing lead in the blood, but is not effective in removing lead which has penetrated the cells.

Furthermore, it is not possible to target specific organs with conventional chelation therapy. Certain metals are more significantly deposited in certain organs than in other organs. Some metals, for example, are significantly deposited in the bone. Thus, in order to provide an effective treatment it is necessary to have a substance which can penetrate the cellular barrier lining the bone surface. This capability is not readily available with conventional chelating agents.

As mentioned above, chelation therapy has other serious limitations. Injections are painful and difficult, particularly when it is necessary to treat children. Repeated treatments are often required. Because of the fact that only metal found in the blood is effectively removed, timing of the treatments is critical.

Accordingly, it would be a significant advancement in the art to provide methods and compositions for treating metal poisoning and contamination which overcame many of the limitations of the conventional art. Specifically, it would be a significant advancement in the art to provide compositions for treating metal poisoning which could be administered orally. It would be an advancement in the art to provide a chemical composition for the treatment of metal poisoning which was sufficiently lipophilic to facilitate passage of the composition across the intestine and across tissue and cellular barriers.

It would be a further significant advancement in the art to provide compositions for the treatment of metal poisoning which could be directed to remove specific metals. It would be another advancement in the art to provide compositions which could target specific organs or sets of organs. It would be a related advancement in the art to provide synthesis parameters for synthesis of compositions which could accomplish targeting of specific metals in specific organs.

Such methods and apparatus are disclosed and claimed herein.

BRIEF SUMMARY AND OBJECTS OF THE INVENTION

The present invention is related to methods and compositions for the decorporation of heavy metals. The present invention represents a significant advancement in that it discloses materials which are capable of removing metals from the body of warm blooded mammals, and specifically humans, but are at the same time significantly lipophilic and capable of oral administration. The present invention also teaches the tailoring of the chemical compositions such that specific metals may be targeted and specific organs and tissues will receive increased concentrations of the composition.

The present invention is effective in decorporation of a wide variety of metals. For purposes of this application, these are defined as metals of groups II-A, III-B, IV-B, V-B, VI-B, VIII, I-B, II-B, III-A and IV-A of the periodic table (CAS Version). Also included are the actinides and lanthanides. Examples of such metals are: aluminum, barium, calcium, cadmium, cerium, chromium, cobalt, einsteinium, gallium, hafnium, iron, indium, lanthanum, lead, manganese, mercury, nickel, samarium, thorium, tin, titanium, uranium, yttria, zinc and zirconium. It will be appreciated from the discussion below, that the present invention is applicable to decorporation of a wide spectrum of metals.

The compositions of the present invention generally comprise chelators which are transformed in such a manner as to modify the balance between hydrophilic and lipophilic characteristics. In this process the chelator may be modified by the attachment of groups that promote active transport of the molecule across the intestinal wall. Such groups may include carbohydrates, glycosides, etc.

The ligands preferably consist of O or O,N donors for type "A" metals. Type "A" metals are metals having an outer electron shell supplemented to 8 electrons. Polyaminocarboxylic acids (PACA) are examples of this group. Alternatively, the ligands should be O-N-S (or P) donors for metals having shells supplemented to 18 electrons ("B" metals). DMPS, BAL (British Anti-Lewisite, Dimercaprol) and Desferrithionin are examples of O-N-S donor chelators.

These chelators can be substituted in the same way as is shown below for PACA. In addition, the PACA's can be modified such that one or more of the secondary amino groups are replaced by sulfur. In this case, the diethylenetriamine (DT) or triethylenetetramine (TT) in the first step of the synthesis illustrated below would be replaced by thio- or dithio- polyamines.

As mentioned above, a currently preferred group of ligands within the scope of the present invention are the partially lipophilic polyaminocarboxylic acids (PACA). In some embodiments of the invention, the PACA's are synthesized in non-aqueous media from triethylenetetramine (TT) by monoalkylation of a primary amino group. This is followed by exhaustive carboxymethylation of the remaining amino groups using ethylbromoacetate and subsequent alkaline hydrolysis of the ester. Characterization and analysis of these materials in conjunction with heavy metals have shown these substances to be strong chelating agents similar to EDTA or DTPA. For example, these compounds have been found to be capable of removing plutonium from contaminated liver cytosol in vitro.

In contrast to their non-lipophilic counterparts EDTA and DTPA, however, the chelating agents within the scope of the present invention exhibit appreciable absorption from the intestine. Therefore, these chelating agents are capable of being administered orally. In addition, with increasing length of the alkyl chain, the chelons can be directed primarily to the liver, one of the target organs for actinide contamination.

As mentioned briefly above, the compositions of the present invention are capable of modification based upon the particular metals which are targeted and the specific organ in which those metals tend to accumulate. For example, the side chain attached to a PACA can be modified to provide the compound with the desired characteristics. Classes of side chain molecules which fall within the scope of the present invention would include (but would not be limited to) alcohols, alkyl groups, carbohydrates, carboxylic acids, and alkylphosphoric acids. One example of such a modification would be the use of an alkylphosphoric acid side chain attached to a lipophilic or partially lipophilic PACA. Modified PACA's of this type are taken up by the liver. Thus, if the metal of interest accumulates in the liver (such as americium) the modified PACA described above would be well suited for the treatment of americium poisoning.

DETAILED DESCRIPTION OF THE PREFERRED EMBODIMENTS

Figure 1A:
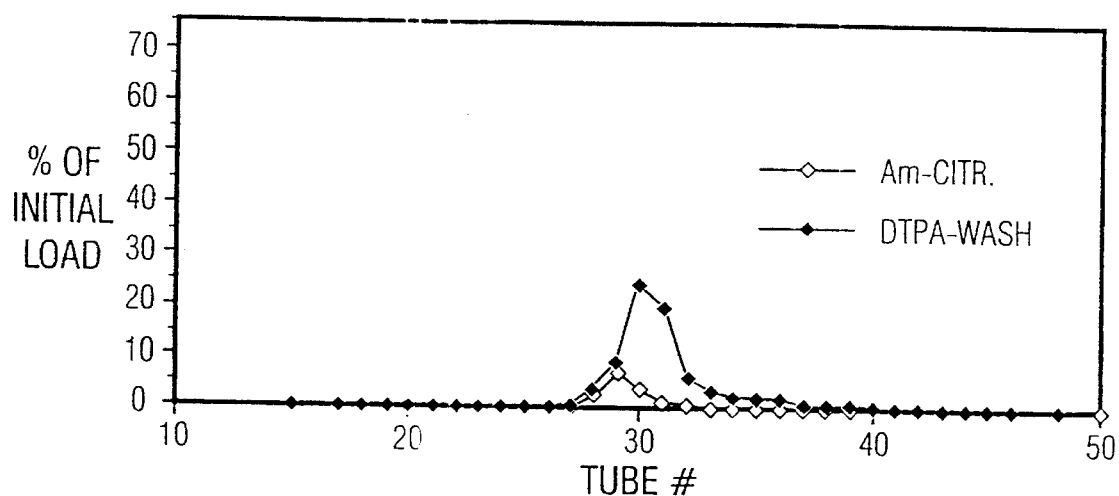
FIG. 1(a) is an elution spectrum of Am-Citrate followed by DTPA wash.

The present invention is related to modified chelators which are suitable for oral decorporation therapy in the treatment of heavy metal poisoning and contamination in warm blooded mammals, including specifically humans. The compositions of the present invention comprise linear polyaminocarboxylic acids which are monosubstituted by various chemical species. The monosubstituted species may, for example, include alkyl groups of varying chain lengths, straight or branched chain fatty acids, alcohols, carbohydrates, carboxylic acids, alkylphosphoric acids, or other substituents which include metabolizable natural compounds. Alternatively, other chelating agents may also be modified in a similar manner to accomplish the objectives of the invention. Such other chelators include, but are not limited to, dimercaptopropanesulfonate (DMPS), British-Antilewisite dimercaptopropanol (BAL), and desferrithionins.

The compositions of the present invention are generally found to be strongly absorbed from the intestine. As mentioned above, the compositions can also be targeted to specific organs and are capable of entering the cell because of the partially lipophilic nature of the compositions. The compositions of the present invention are capable of forming stable chelates with a variety of heavy metal ions.

As mentioned above, the present invention is suitable for use in the treatment of a wide variety of heavy metals. Such metals, especially heavy metals, include the metals of Groups II-A, III-B, IV-B, V-B, VI-B, VII-B, VIII, I-B, II-B, III-A and IV-A of the periodic table (CAS Version), as well as the actinides and lanthanides. Examples of such metals are: aluminum, barium, calcium, cadmium, cerium, chromium, cobalt, einsteinium, gallium, hafnium, iron, indium, lanthanum, lead, manganese, mercury, nickel, samarium, thorium, tin, titanium, uranium, yttria, zinc and zirconium.

The existence and effectiveness of the modified chelators according to the present invention has been verified experimentally. Specifically, column chromatography has verified the existence of certain of the subject chelates. In animal experiments, it has been found that when given orally to rats, the compounds efficiently reduced well fixed heavy metal burdens without redistribution of the metal. Excretion of the metal alkyl chelates occurs via urine or bile, and feces depending on the type of substitution moieties. Significant elimination of the heavy metals from both the liver and bone has been observed.

The compositions of the present invention fall within the scope of several selection criteria. The first criterion is that the composition is partially lipophilic in character. As mentioned above, a major drawback of existing chelators used for decorporation is that they are strongly hydrophilic. As a result they have little ability to penetrate across tissue and cellular barriers. Strongly hydrophilic chelators are also rapidly excreted and thus require frequent administration.

The compositions of the present invention are selected such that they are partially lipophilic. As a result, good cell penetration is observed. In addition, these chelators are not as rapidly eliminated and, therefore, do not require as frequent administration.

Another important criterion is that the composition form heavy metal complexes at physiological pH. Without this ability it is clear that poor performance will be experienced. The compositions disclosed as part of the present invention are in fact found to form stable complexes within the range of physiological pH.

Furthermore, it is important that the complexes formed by the bonding of the metal to the composition be less toxic than the free metal ion. Clearly, if the complex formed is as toxic or more toxic than the subject metal itself, little has been accomplished. In the present invention it is found that the disclosed compositions also meet this criterion.

It is also important that the compositions within the scope of the present invention be modified in such a manner that they are targeted to specific tissues within the body of the warm blooded mammal. As mentioned above, this is achieved by monosubstitution of the polyaminocarboxylic acid or other electron donor moiety. Essentially, the species added to the polyaminocarboxylic acid is similar in properties to other chemicals in the subject tissue. Thus, a natural affinity and targeting effect is achieved.

Tissue targeting is important because heavy metal distribution within the body is also tissue specific. At the same time the tissue in which the metal resides may change over time. For example, americium is initially found in the liver, but as time progresses, it accumulates in the bone. Thus, targeting the specific tissue at the appropriate time is of importance. At a certain time following contamination or poisoning, a composition which targets the liver may be used. If treatment occurs later, a composition which targets bone may be preferred.

It is also of importance that the compositions promote decorporation of the metal, not redistribution of the metal. In some studies with known chelation therapy agents it has been suggested that the metal is simply dislodged from one tissue and redeposited in another tissue. The compositions of the present invention, conversely, result in actual removal of the metal from the body of the mammal.

Another criterion for selecting the chelating agents of the present invention is that they have a greater affinity for the targeted heavy metals than for calcium, zinc or other essential trace metals (even though the compositions may also be used to remove these elements if desired). Calcium is readily available in tissue fluids, and a high binding affinity for calcium may render the composition ineffective in most applications. Binding of endogenous zinc could also render the composition ineffective in most cases and may cause additional physiological problems due to the depletion of an important necessary trace element. Thus, for most applications, it is important that the composition have a greater affinity for metals other than calcium, zinc or other essential trace elements.

Finally, in selecting the materials within the scope of the present invention it is important that they be capable of easy administration, preferable oral administration. As discussed above, most known agents used in chelation therapy are highly hydrophilic and require parenteral administration. The present invention is an advancement over presently used chelating agents in this regard because the partially lipophilic agents of the present invention are capable of oral administration.

In certain embodiments, the present invention teaches the synthesis of new compounds with chelation characteristics similar to EDTA and DTPA but different pharmacological properties that eliminate the obstacle of parenteral administration and poor cellular penetration and short residence time in the tissue.

These new chelators, including partially lipophilic PACAs, also pass the intestinal barrier, and thus, they can be given orally. The compounds appeared to penetrate the sites of primary metal deposition which are, in part, intracellular. They complex with the actinides, are excreted without redeposition in other organs, such as the kidneys, and have no obvious signs of toxicity.

Commonly in the past, carboxymethylation of the alkyl substituted amine obtained in the first step of the synthesis was carried out in aqueous media using digestion with bromoacetic acid at a basic pH. Generally, the products are not well defined and are extremely difficult to purify. For most purposes, therefore, the resulting material is not suitable for in vivo use.

The nonaqueous synthesis method described in this application produced the desired compounds with a reasonable yield and in the highly purified form that made both a rigorous chemical characterization and in vivo testing possible.

Two of the compounds described in additional detail in this application, $C_{12}TT$ and $C_{22}TT$, are only representative of a series of PACAs with chain lengths ranging from $C_6$–$C_{22}$ that have been synthesized from triethylenetetramine (TT) and diethylenetriamine (DT). As mentioned above, PACA's are only one group of modified chelators within the scope of the invention.

Due to the availability of two additional donor groups, chelators synthesized from TT proved to be stronger for the 8-coordinate Am than those based on DT. However, DT derivatives are believed to have therapeutic advantage on certain other types of metal deposits.

Altering the length of the alkyl side chains and consequently the lipophilicity of the chelators is expected to change several of their pharmacological properties. Data suggest that the length of the alkyl chain will influence the intestinal absorption of the compounds, their selective uptake by individual organs or tissues and their transport across cellular and subcellular membrane barriers. This property may be used to direct the compounds to metal depot sites in the cell. This is important, for instance, as actinide deposits in the liver are known to be located initially in the hepatocytic ferritin with subsequent migration to secondary lysosomes and then to macrophages associated with sinusoidal lining cells.

It is expected that for fresh deposits of metals, compounds with shorter side chains may be more effective, whereas removal from lysosomes and macrophages may be more effective using longer chain, micelle-forming compounds.

EXPERIMENTAL SYNTHESIS AND USE OF INVENTION

The effectiveness of the oral administration of two tested model compounds within the scope of the present invention, $C_{12}TT$ and $C_{22}TT$, to remove aged Americium (Am) deposits from the body of warm blooded mammals was demonstrated in a rodent model. The power of these chelons to greatly accelerate the removal of established deposits of Am by this route of administration relates to their ability to traverse cellular barriers and membranes. It is currently believed that the longer side chains are more readily incorporated into the liver. As discussed above, such a mechanism may also help explain the greater loss of Am from the bone, where the longer side chain apparently increase the uptake of the chelator by bone marrow macrophages, also a site of Am deposition. The use of an oral chelator offers considerable improvement over existing methods.

In the doses given, which were remarkably effective in accelerating the removal of established deposits of Am from the body, there were no obvious toxic reactions to the chelators. There were no significant differences in body weights and no overt histological evidence of pathological damage to the tissues. This is in contrast to expectations based on the destruction of the epithelial lining and related structures of the intestinal tract followed by death after frequent parenteral administration of Ca DTPA in dogs as observed by Taylor, et al., *Effects of ethylenediamine tetraacetate and diethylenetriaminepentaacetate on DNA synthesis in kidney and intestinal mucosa of folate treated rats.* Biochem. Pharmacol. 1972, 21, 3313–3315.

As mentioned above, some of the compounds of interest comprise diethylenetriamine (DT) or triethylenetetramine (TT) based molecules which are then terminally alkylated with increasing chain lengths. As mentioned briefly above, the synthesis of these compounds is done in several steps. First, the respective amines are mono-alkylated with 1-bromo-alkyls and the terminally alkylated amines are separated. This is followed by exhaustive carboxymethylation with bromo-acetic acid ethyl ester in the presence of triethylamine and finally hydrolysis of the ester with a strong base. Final purification at each step may be by flash chromatography or liquid crystallization. Purity for the final products was typically >80% as determined by each compound's Ca-equivalent.

The general scheme of the synthesis is outlined as follows:

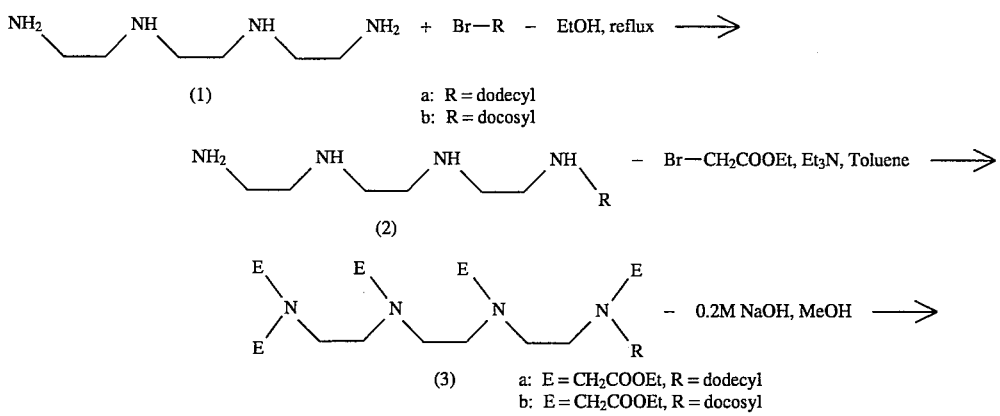

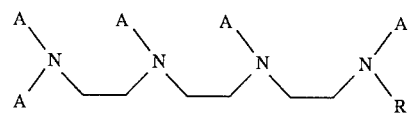

(4)  a: A = CH₂COOH, R = dodecyl
     b: A = CH₂COOH, R = docosyl

For new compounds, thin layer chromatography using Silica Gel sheets on polyester film was performed and Rf values for several solvent systems, the nD20, mp., a NMR spectra and IR spectra were determined. In addition, mass spectra were taken using MATT 112S or MATT 731 spectrometers at 7 kV. Relative peaks were determined for the mass range between 50 and 800 units. The data agreed with the masses of the theoretically expected fragment radicals.

For each compound, pH-titrations in both directions were carried out at constant ionic strength. All compounds were completely protonated between pH 7.2 and 7.8 for the DT-series and 7.7 and 8.0 for the TT-series, pointing to the availability of all potential donor electrons derived from carboxyl oxygens—for complex or chelate formation similar to EDTA (pH 8.8) and DTPA (pH 6.7), the two model compounds known for their ability to chelate actinides and some other metals.

To establish the ability of these new compounds to chelate heavy metals, known quantities of the Na-salts of most DT- and TT-based compounds were potentiometrically titrated at constant ionic strength with Ca and Zn ions. The Ca and Zn chelates were chosen for this experiment because EDTA and DTPA commonly are given in this form for chelation. Plots of Delta (Δ)mV vs. meq of metal ion suggest a 1:1 complex similar to EDTA and DTPA. Infrared spectra taken of uncomplexed compounds, and Ca and Zn complexes showed defined shifts of absorption peaks and changes associated with formation of metal chelate.

The chemical structure of two possible DT- and TT- based chelons is illustrated as follows:

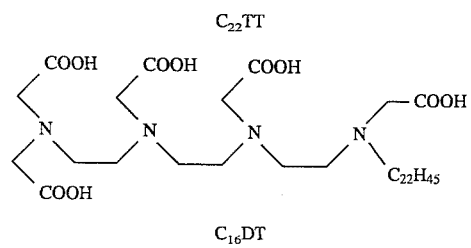

$C_{22}TT$ $C_{16}DT$

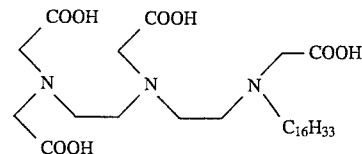

Prior to initiating biological studies, additional characteristics of these chelons were evaluated. The compounds and equivalent quantities of EDTA or DTPA were reacted at physiological pH with $^{241}$Am and the resulting complexes were applied on top of 80 cm columns packed with Sephadex G-25. Likewise, the same amount of Am-citrate was applied. Elution spectra of Am were compared. Because of the dilution of the citrate during the run, Am originally applied as the citrate complex hydrolyzed, remained on the column and had to be eluted with DTPA. In all other cases, the Am complex was recovered in high yield from the column. Elution positions of combinations of Am complexes with compounds were at least of the strength of the EDTA complex, whereas the DTPA complexes were sometimes stronger.

Data suggest that the partially lipophilic chelons of the present invention have greatly improved pharmacokinetic properties over traditional chelators, such as EDTA and DPTA. To test the ability of complexed chelons to move across membrane and cellular barriers, an assay has been developed that measures the intestinal passage of the chelons in closed duodenal segments in situ over a 3 hour period. It is found that $^{241}$Am complexed chelons of the TT series have substantial movement across this barrier, when compared with uncomplexed $^{241}$Am. Although there were differences in the rate at which some of these compounds moved through this tissue barrier, all were effective in Am removal in vivo as set forth in the following Table 1.

TABLE 1

Effect of 1 week feeding of TT-based chelons on total body and liver content of $^{241}$Am. Am was allowed to incorporate for 1 week prior to oral chelon feeding. Total body counts were taken before and after chelon feeding. Liver values were determined at necropsy.

| Compound | % Reduction in total body $^{241}$Am. (Before vs after chelon feeding) | % Reduction in liver $^{241}$Am. (Compared with controls) |
|---|---|---|
| Control | −27.2 ± 2.3 | — |
| C₈TT | −39.0 ± 6.3 | −30.1 ± 10.0 |
| C₁₂TT | −46.5 ± 4.0 | −57.1 ± 0.1 |
| C₂₂TT | −45.7 ± 6.1 | −47.9 ± 9.1 |

In vivo decorporation testing indicates that the compounds within the scope of the present invention have considerable activity when given orally in reducing total body concentrations of $^{241}$Am deposits. This is further illustrated by Table 2 below. The substantial reductions in liver burdens are particularly relevant because most $^{241}$Am is initially deposited in the liver and later distributes to the skeleton.

TABLE 2

REDUCTION OF $^{241}$Am ORGAN BURDEN BY ORAL CHELON ADMINISTRATION[a]

| ORGAN | $C_{12}$TT - TREATED | | $C_{22}$TT - TREATED | |
|---|---|---|---|---|
| | % REDUCTION | p-VALUE | % REDUCTION | p-VALUE |
| WHOLE BODY | 29 | <0.001 | 44 | <0.001 |
| CARCASS | 20 | <0.001 | 36 | <0.001 |
| BOTH FEMORA | 17 | <0.001 | 32 | <0.001 |
| LIVER | 71 | <0.001 | 89 | <0.001 |
| ONE KIDNEY | 24 | >0.1 | 26 | >0.1 |

[a]Reduction = 100 × 1-(% of initial activity in treated rats at death/% of initial activity in controls at death); 9 Rats/Group; 10 Days Treatment.

Synthesis of other chelons

While much of the description contained herein has focused on the DT- and TT-based compounds, several other classes of chelons fall within the scope of the invention. For example, a series of alkyl carboxylated compounds (K-series) having the following general structure have been synthesized.

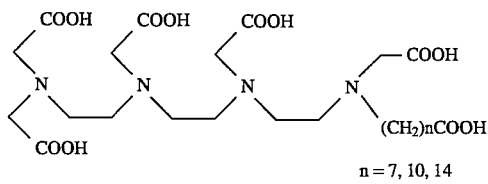

n = 7, 10, 14

Some of the properties of these chelons have been determined and are set forth in Table 3 below.

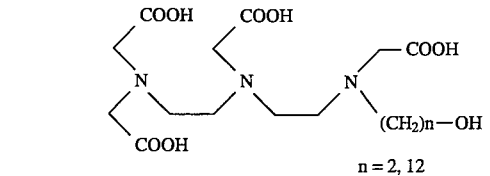

n = 2, 12

Since different metals and nuclides preferentially deposit in different tissues it is necessary to have the capability to varying the chemical characteristics of the chelon used. In most cases, the internal deposition of the metal will also change with time. For example, Am is initially deposited mostly in the liver, but with time these deposits will translocate to the skeleton in humans and experimental animals. Monomeric Pu, for example, is incorporated mostly in osseous tissues, but polymeric Pu is also incorporated in the

TABLE 3

| | Base | | HCL salt | | | Base | | HCL salt | |
|---|---|---|---|---|---|---|---|---|---|
| Chelon | Yield | nD | yield | mp | Chelon | Yield | nD | yield | mp |
| K8D | — | — | — | — | K8T | — | — | — | — |
| K11D | 68 | — | 63 | 213 | K11T | 60 | — | 24 | 220 |
| K15D | — | — | 98 | — | K15T | 99 | — | 52 | — |
| K8DE | — | — | — | — | K8TE | — | — | — | — |
| K11DE | 29 | 1.466 | — | — | K11TE | 49 | 1.472 | — | — |
| K15DE | 47 | 1.466 | — | — | K15TE | 18 | 1.470 | — | — |
| K8DT | — | — | — | — | K8TT | — | — | — | — |
| K11DT | — | — | 57 | — | K11TT | — | — | 48 | 140 |
| K15DT | — | — | 75 | 146 | K15TT | — | — | 37 | — | mp = melting point.
nD = optical refraction.
Purity of all compounds was greater than 80% (usually >90%).

In addition, alcohols also fall within the scope of the present invention. One class of alcohols has the following structure:

mononuclear phagocyte system. By the addition of selected chemical moieties on the PACA-based compounds, improved organ targeting is achieved. This offers considerable therapeutic advantage for decorporation for a variety of metals and nuclides.

Polyaminocarboxylic acid derivatives with sugar moieties are expected to improve targeting of the chelon to skeletal tissues and other tissue and cellular compartments rich in sugars. Two approaches to synthesize these compounds are presently preferred. In the first approach, N-D-glycosylamines are synthesized. The sugar is bound with polyamine via a glycosyl C-N bond, i.e.:

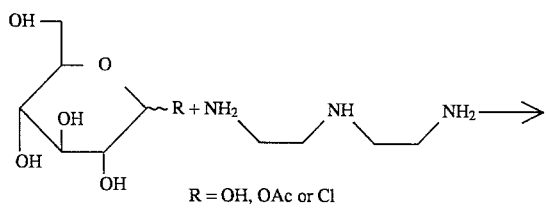

R = OH, OAc or Cl

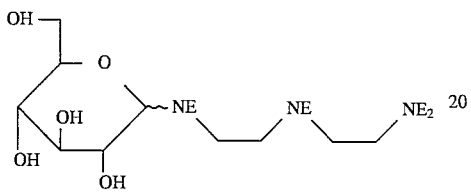

E = CH$_2$COOEt or CH$_2$COOH

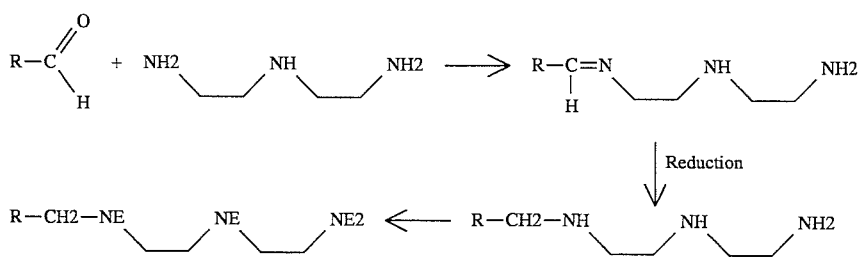

This reaction is carried out by substitution of hydroxyl, acetoxyl or chlorine in sugar derivatives with DT or TT amine groups, followed by carboxymethylation and hydrolysis. The C-N glycosidic bond can be unstable under basic conditions and may undergo hydrolysis. In this event the bond is protected by starting with polyamines having electron acceptor substituents, such as an acetyl group.

In the second method O-D-glycosides are synthesized instead of CN-glycosides by binding the sugar with polyamine via glycosyl C-O bond and alkoxy chain, i.e.:

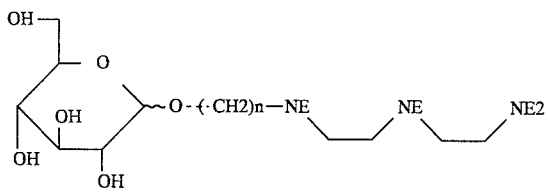

n = 2 or 12
E = CH2COOEt or CH2COOH

The sugar is bound to DT or TT via a short ethoxy chain (n= 2 or 3) or via a long alkoxy chain (n= 12) to preserve the partially lipophilic character of the chelon. This is done by the synthesis of appropriate hydroxyalkyl DT and TT polyacetic acid ethyl esters and coupling with chlorosugars in the presence of HgCN and CaSO$_4$ as a drying agent in benzene.

Incorporation of some natural products, analogous to endogenous substances, into the chelon improves tissue penetration, distribution and localization. This class of chelons is expected to improve localization to liver and other soft tissues. Phytol and retinol may be used as natural alcohols, then oxidized with pyridinium chlorochromate or manganese dioxide to yield the aldehydes, phytal and retinal. These aldehydes and pyridoxal-phosphate undergo reductive amination with DT or TT polyamines using sodium cyanoborohydride. The compounds are then carboxymethylated followed by hydrolysis. The general reaction is as follows (beginning with the aldehyde):

Other compounds within the scope of the present invention include potyaminocarboxylic acid derivatives with imidazole, benzimidazole and histamine moieties. In addition to improving tissue penetration, histamine itself has chelation properties. Imidazole derivatives are quite acidic and may help eliminate problems arising from the slight detergent properties encountered in noncarboxylated straight chain compounds.

Another group of compounds within the scope of the present invention includes polyalkyl phosphonic derivatives. Phosphono groups have an enhanced tendency for complex formation and various phosphonic acid compounds are used as targeting agents for skeletal imaging and certain skeletal diseases. These compounds localize on bone surfaces (similar to Pu and Pb, for example) and are expected to enhance the decorporation of actinide and lanthanide, and other elements deposited in bone. The synthesis of methylenephosphonic acid derivatives is done by established methods using methylphosphonyl chloroether and appropriate DT and TT derivatives using phosphorus trichloride and formalin. Alkylphosphates of DT and TT are also synthesized via phosphorylation from previously prepared alkylhydroxy derivatives using dibenzyl phosphorochloridate or monosubstituted phosphoric acid in the presence of 2,4,6-triisopropylbenzenesulphonyl chloride.

Thus, it can be seen that the present invention teaches a variety of compounds. Each compound has particular characteristics that are beneficial in particular situations. Using the present invention it is possible to provide a chelating agent which targets particular types of tissues. Since most heavy metals accumulate in particular tissues, it is important to provide a chelating agent which targets the same tissues. At the same time, chelating agents which form complexes with particular metals are provided.

EXAMPLES

The following Examples are given to illustrate various embodiments which have been made or used, or which may be made or used in accordance with the present invention. These examples are given by way of illustration only, and it is to be understood that the examples are not intended to be comprehensive or exhaustive of the many types of embodiments of the present invention.

Example 1

Several new bifunctional agents have been synthesized based structurally on triethylenetetramine (TT) containing a single unbranched alkyl group of various chain lengths. The notation for these compounds used in this text is CnTT, where n denotes the number of carbon atoms in the alkyl chain. Several methods for the preparation of alkyl, acyl or aryl derivatives, not necessarily monosubstituted, of polyethyleneamines have been reported and are available in the art. Monoalkylation of a single primary amino group of triethylenetetramine followed the same principle by reacting a large excess of the amine in absolute alcohol with the alkylhalide.

This was followed by carboxymethylation of the product using ethyl bromoacetate with triethylamine as a base for binding the hydrogen bromide produced during the reaction. The resulting ester was then hydrolyzed to the respective polyaminocarboxylic acids. The carboxymethylation reaction was carried out at room temperature with toluene as the solvent. The choice of using the bromoethylester for the carboxymethylation instead of a haloacetic acid was very important because the products were dissolved in organic solvents and were easily purified using flash chromatography. It has been found that, the success of preparing these compounds in a pure and well characterized state depends on the application of a nonaqueous scheme of synthesis. Synthesis of homologues with chain length between 8 and 22 carbon atoms follows the same principles.

Melting points were determined on a Reichert hot stage apparatus. Flash chromatography on silica gel was used for purification. Thin-layer chromatography was performed using polyester sheets with silica gel 60 F254 and the following solvent mixtures:

A) chloroform, methanol, propanol, ammonia 5:2:2:1

B) chloroform, benzene, propanol, methanol, ammonia 290:100:12:2:1

C) propanol, ammonia, water 5:1:1

D) chloroform, hexane 1:1

E) chloroform, benzene, propanol, methanol, ammonia 690:100:12:2:1

Compounds were characterized using IR, NMR and MS spectroscopy. Infrared spectra were obtained from KBr discs or films using a Beckman 2100 spectrometer. The proton NMR spectra were recorded on an IBM NR200 spectrometer in deuteriochloroform ($CDCl_3$) with tetramethylsilane as an internal standard or in deuterium oxide containing some NaOD at pH 13. FAB-Mass Spectra at 7 kV were determined in xenon gas using a Matt 112 S or Matt 731 masspectrometer. All samples were dissolved in glycerol/ammonia.

For the preparation of the Ca and Zn complexes, the title compounds were dissolved in base to give a solution between pH 7.4 and 8 and an equivalent amount of $CaCl_2$ or $ZnCl_2$ was added. The necessary quantity of $Ca^{++}$ or $Zn^{++}$ had been determined by prior titration of an atiquot of the chelator with these metal ions in the presence of Cal-Red as the indicator. This amount corresponded to a 1:1 chelate. The resulting complex was crystallized, dried and used in $D_2O$ to obtain the desired IR spectra.

Example 2

In this Example 1-N-Dodecyl-Triethylenetetramine (N-Dodecyl-3,6-diazaoctane-1, 8-diamine) was synthesized and characterized using the procedures set forth in Example 1.

Triethylenetetramine (10.4 g, technical grade 70%, 50 mmol) was dissolved in 50 mL of ethanol, and dodecylbromide (2.5 g, 10 mmol) was added dropwise at room temperature. Excess of triethylenetetramine serves as the base necessary for trapping hydrogen bromide released during the reaction. The reaction mixture was refluxed for 4 hours and then evaporated to dryness in vacuo. The oily residue was mixed with 20 ml of 1-butanol and 20 ml of toluene and washed with water. The two phases were separated, the organic layer was dried over sodium sulfate, and the solvents were evaporated. The residue was dissolved in methanol and the $C_{12}$-amine precipitated with HCl. The hydrochloride was finally crystallized from wet methanol to yield 2.1 g (45%) of white crystals of the HCl salt of 2a: mp 220°–222° C.; TLC (A) $R_f$=0.38. Anal. ($C_{18}H_{42}N_4$·4HCl) C, H, N; Ci: calcd, 30.87; found, 30.07. The following $^1$H NMR ($CDCl_3$) spectrum was obtained: alkyl chain protons (($CH_2$)$_{11}CH_3$), δ 0.8–1.6 (m, 30 H); 5 amine protons ($NH_2$ or=NH), 12 ethylene protons ($CH_2CH_2$), δ 2.5–2.8 (m, 12 H).

Example 3

In this Example 1-N-Docosyl-Triethylenetetramine (N-Docosyl- 3,6-diazaoctane-1, 8-diamine) (2b) was synthesized and characterized using the procedures set forth in Example 1.

The reaction was carried out as for 2a, using triethylenetetramine (1) (52.2 g, 70%., 250 mmol), EtOH (200 mL) and docosyl bromide (19.45 g, 50 mmol). Crystallization of the hydrochloric acid salt of 2b from aqueous MeOH (75%) yielded 12.0 g (40%) of colorless crystals: mp 216°–219° C.; TLC (A) $R_f$=0.49. Anal. ($C_{28}H_{62}N_4$·4HCl) C, H, N, Cl. The $^1$H NMR ($CDCl_3$) spectrum was composed of the following: alkyl chain protons (($CH_2$)$_{21}CH_3$), δ 0.8– 1.6 (m, 45H); 5 amine protons ($NH_2$ or NH), 12 ethylene protons ($CH_2CH_2$), δ 2.5–2.8 (m, 12H).

Example 4

In this Example 1-N-Dodecyl-triethylenetetramine pentaacetic acid pentaethyl ester (Pentaethyl N-Dodecyl-3,6-diazaoctane -1,8-diamine-N,N',N',3,6 -pentaacetate) (3c) was synthesized and characterized using the procedures set forth in Example 1.

Ethyl bromoacetate (75.0 g, 450 mmol) was added dropwise at room temperature to a mixture of 1-N-dodecyltriethylenetetramine hydrochloride (2a) (20.6 g, 45 mmol), triethylamine (50.8 g, 503 mmol), and 400 mL of toluene. The triethylamine again serves as the base necessary for trapping released hydrogen bromide; it does not react with the dodecyl bromide. This mixture was stirred for 24 hours. The resulting soft solid, which consisted mostly of triethylamine-HBr, was filtered off and washed with 50 mL of chloroform. Solvents from the combined filtrates were evaporated under reduced pressure and the residue was again dissolved in chloroform and washed with water. After drying over sodium sulfate, the chloroform was evaporated. The product was, finally, purified by flash chromatography (eluting successively with solvent D, chloroform, and solvent E) and obtained as a colorless oil (8.3 g, 25%) of (3a): $n^{20}_D$=1.4850; TLC (B) $R_f$=0.53; IR (film) 1734, 1462 cm$^{-1}$ corresponding to the ester and amino groups. Anal. ($C_{38}H_{72}N_4O_{10}$) C, H, N. The following $^1$H NMR (CDCl$_3$) spectrum was obtained: alkyl chain protons (($CH_2$)$_{11}$CH$_3$), δ 0.84–1.43 (m, 25 H) ; methyl protons of five ester groups (OCH$_2$CH$_3$), δ 0.84–1.43 (m, 15 H); protons of one methylene group (NCH$_2$CH$_2$N-alkyl) δ 6 2.59 (t, 2H, J=7.9 Hz); protons of five methylene groups (NCH$_2$CH$_2$N) 67 2.75–2.84 (m, 10 H); methylene protons of acetic acid residue (NCH$_2$COOEt) δ 3.39 (s, 2 H), 3.45 (s, 2 H), 3.46 (s, 2 H), 3.57 (s, 4 H); methylene protons of five ester groups (OCH$_2$CH$_3$) δ 4.09–4.21 (m, 10 H) .

The methylene protons of carboxymethyl groups were observed as four singlets: three as two proton signals and only one as a four proton signal. This indicates that the alkyl group of 3a binds to the terminal nitrogen $N^1$. If the alkyl group had been attached to $N^2$, two four proton signals or one eight proton signal should be observed. The two proton signal at 2.59 ppm, separated from the pattern of methylene protons of the trimethylenetetramine chain, confirmed the proposed structure of a terminally attached alkyl group. Only one methylene group has a different attachment and is shifted upfield.

Example 5

In this Example 1-N-Docosyl-triethylenetetramine pentaacetic acid pentaethyl ester (Pentaethyl N-Docosyl-3,6-diazaoctane-1, 8-diamine-N,N',N',3,6-pentaacetate) (3b) was synthesized and characterized using the procedures set forth in Example 1.

1-N-Docosyltriethylenetetramine hydrochloride (12 g, 20.0 mmol) and ethyl bromoacetate (33.4 g, 200 mmol), in toluene (200 mL) and triethylamine (28.3 g, 280 mmol) were stirred at room temperature for 4 days. Then the temperature was raised to 40° C. and agitation was continued for an additional 3 hours. The reaction mixture was separated by flash chromatography (using successively the solvents: D, chloroform, and finally solvent E), and the product (3b) purified by crystallization from a mixture of MeOH and ether: yield 9.4 g (53.0%); mp 82°–83° C.; TLC (B) $R_f$=0.49; IR (film) 1730, 1462 cm$^{-1}$ . Anal. (CH$_{48}$H$_{92}$N$_4$O$_{10}$) C, H, N. The proton NMR spectrum corresponded to that of (3a) except for the integration of the signal between 0.85 and 1.42 which had a 60-proton multiplet instead of 40 protons. Thus, the following $^1$H NMR (CDCl$_3$) spectrum was obtained: alkyl chain protons ((CH$_2$)$_{21}$CH$_3$) δ 0.85–1.42 (m, 45 H); methyl protons of five ester groups (OCH$_2$CH$_3$) δ 0.85–1.42 (m, 15 H); protons of methylene group (NCH$_2$CH$_2$N-alkyl) δ 2.57 (t, 2 H, J=7.9 Hz); protons of five methylene groups (NCH$_2$CH$_2$N) δ 2.73–2.84 (m, 10 H); methylene protons of acetic acid residue —NCH$_2$COOEt δ 3.36 (s, 2 H) , 3.43 (s, 2 H) , 3.45 (s, 2 H) , 3.57 (s, 4 H); methylene protons of five ester groups (OCH$_2$CH$_3$) δ 4.09–4.21 (m, 10 H). Again, the alkyl group was attached to the terminal nitrogen.

Example 6

In this Example 1-N-Dodecyl-triethylenetetramine pentaacetic acid, $C_{12}$TT, (N-Dodecyl-3,6-diazaoctane-1,8 -diamine-N,N',N',3,6-pentaacetic acid) (4a) was synthesized and characterized using the procedures set forth in Example 1.

The dodecyl ester (3a), (1.2 g 1.7 mmol) was dissolved in 19 mL of MeOH, and aqueous 2M NaOH (15 mL) was added in small portions. The reaction mixture was stirred at room temperature for 1 h, acidified with concentrated HCl, and left overnight in the refrigerator. The product 4a was filtered off and crystallized from wet MeOH as colorless crystals (0.8 g, 82%): mp 202°–203° C.; TLC (C) $R_f$=0.45; IR 1730, 1630 cm$^{-1}$, indicating partially protonized carboxyl groups; mass spectrum, (M$^+$–1) 603. The fragments observed were consistent with the molecular structure of the title compound above (4a). Anal. ($C_{28}H_{52}N_4O_{10}$·4HCl) C, H, N; Cl: calcd, 18.93; found, 18.06. $^1$H NMR (NaOD/D$_2$O, pH=13): alkyl chain protons ((CH$_2$)$_{11}$ CH$_3$) δ 0.77–1.16 (m, 25 H); protons of ethylene groups (NCH$_2$CH$_2$N) δ 2.4 (br s, 12 H); methylene protons of acetic acid residue (NCH$_2$COO$^-$) δ 2.94 (br s, 10 H). $^{13}$C NMR (NaOD/D$_2$O, pH=13 ): alkyl chain carbons ((CH$_2$)$_{11}$CH$_3$) δ 16.6, 25.1, 31.9, 34.3; carbons of ethylene groups (NCH$_2$CH$_2$N) δ 53.5, 54.2, 54.7; methylene carbons of acetic acid residue (NCH$_2$COO$^-$) δ 57.2, 60.8, 61.4, 61.8; carboxylic carbons of acetic acid residue (NCH$_2$COO$^-$) δ 173.8, 181.7, 181.6, 182.2.

Methylene carbons of five carboxymethyl groups were observed as four signals, with one shifted upfield 3.6 ppm. Five carboxylic carbons also appeared as four signals, with one shifted upfield 8.0 ppm. This also confirmed that the alkyl group was bound to $N^1$. If the alkyl group had been attached to $N^2$, two or a maximum of three signals should have been observed at the same region.

Example 7

In this Example 1-N-Docosyl-triethylenetetramine pentaacetic acid, C22TT (N-Docosyl-3,6-diazaoctane-1, 8-diamine-N,N',N', 3,6-pentaacetic acid) (4b) was synthesized and characterized using the procedures set forth in Example 1.

The docosyl ester 3b (1.8 g, 2 mmol) was hydrolyzed at room temperature with 2M NaOH in MeOH (26 mL). After 4 days, water (40 mL) was added and the mixture was acidified to pH 3 with concentrated HCl. The title compound was then crystallized from water, yielding 1.4 g or 92% of 4b: mp 212°–213° C.; TLC (C) $R_f$=0.5; IR 1730, 1630 cm$^{-1}$, indicating partially protonized carboxyl groups; mass spectrum, (M$^+$–1) 743. Again, the fragments observed were consistent with the molecular structure of the title compound (4b). Anal. ($C_{38}H_{72}N_4O_{10}$·4HCl) C, H, N, Cl. $^1$H NMR (NaOD/D$_2$O, pH=13): alkyl chain protons ( (CH$_2$)$_{21}$CH$_3$) δ 0.77–1.16 (m, 45 H); protons of ethylene groups (NCH$_2$CH$_2$N) δ 2.4 (br s, 12 H); methylene protons of acetic acid residue (NHC$_2$COO$^-$) δ 2.94 (br s, 10 H). $^{13}$C NMR (NaOD/D$_2$O, pH=13 ): alkyl chain carbons ((CH$_2$)$_{21}$CH$_3$) δ 6 16.7, 25.4, 32.7, 34.7; carbons of ethylene groups (NCH$_2$CH$_2$N) δ 53.5, 54.1, 54.7; methylene carbons of acetic acid residue (NCH$_2$COO$^-$) δ 57.6, 60.8, 61.4, 61.8; carboxylic carbons of acetic acid residue (NCH$_2$COO$^-$) δ 173.6, 181.1, 182.0, 182.2. This confirmed again that the alkyl group was attached to the terminal nitrogen.

Example 8

In this Example the degree of effectiveness of alkylated PACAs for the removal of Pu, Am, other actinide or perhaps lanthanide elements from the body of warm blooded mammals is studied.

Plutonium and Am have somewhat similar in vivo distribution patterns and, in general, it may be assumed that a decorporation agent may be effective for Pu if found effective for Am, although not necessarily to the same degree.

For most of the in vivo and in vitro studies, Am was selected as the test nuclide because of the convenience of its detection. $^{241}$Am decays by emission of an α particle that is accompanied in 36% of the decay events by emission of a γ ray of 60 keV. The γ-ray permits detection of this nuclide by external γ-counting without further processing of the samples and tissues, an essential requirement for that nuclide determination in the intact animal by whole body counting. However, some in vitro experiments produced specimens of a much smaller mass which, without extensive sample preparation, permitted the determination of alpha-emitting radionuclides by liquid scintillation counting. With those samples, $^{239}$Pu instead of $^{241}$Am was used as the nuclide of primary interest to study the effectiveness of some of the chelators for nuclide removal.

In vitro studies

A number of in vitro tests were performed to ascertain the existence and relative stability of the desired actinide chelates and the necessary pharmacological properties of the new chelons, and to detect signs of overt toxicity. These tests include: a) a comparison of the elution patterns of Am-citrate (a moderately stable complex with $K_1$=7.74 ), $^{241}$Am-EDTA or $^{241}$Am-DTPA (two very stable complexes with $K_1$=16.91 and $K_1$= 24.03, respectively) and $^{241}$Am-$C_{12}$TT (a complex of unknown stability) after gel chromatography on Sephadex G-15, and a comparison of the IR spectra of the open Cn-TT chain with that of the chelate configuration; b) a comparison of the ability of $^{241}$Am-citrate and $^{241}$Am-$C_{12}$TT to pass the intestinal barrier; c) some simple blood tests that were considered useful preliminary indicators of possible chelon toxicity; d) a test for the elimination of Pu from in vivo tagged canine liver cytosol using $C_{12}$TT.

Column chromatography

Gel permeation chromatography was performed on buffer equilibrated, degassed Sephadex G-15 (column size 1.5 cm×85 cm, 0.1N TRIS buffer of pH 7.4 containing 0.01% Na-azide). The void volume was determined by elution of Dextran Blue-2000. Columns were loaded with a known quantity of $^{241}$Am-citrate, $^{241}$Am-EDTA, $^{241}$Am-DTPA, or $^{241}$Am-$C_{12}$TT and eluted under constant hydrostatic pressure with buffer. The $C_{22}$TT compound was omitted from this test because of micelle formation which would have interfered with normal sorption properties.

Figure 1B:
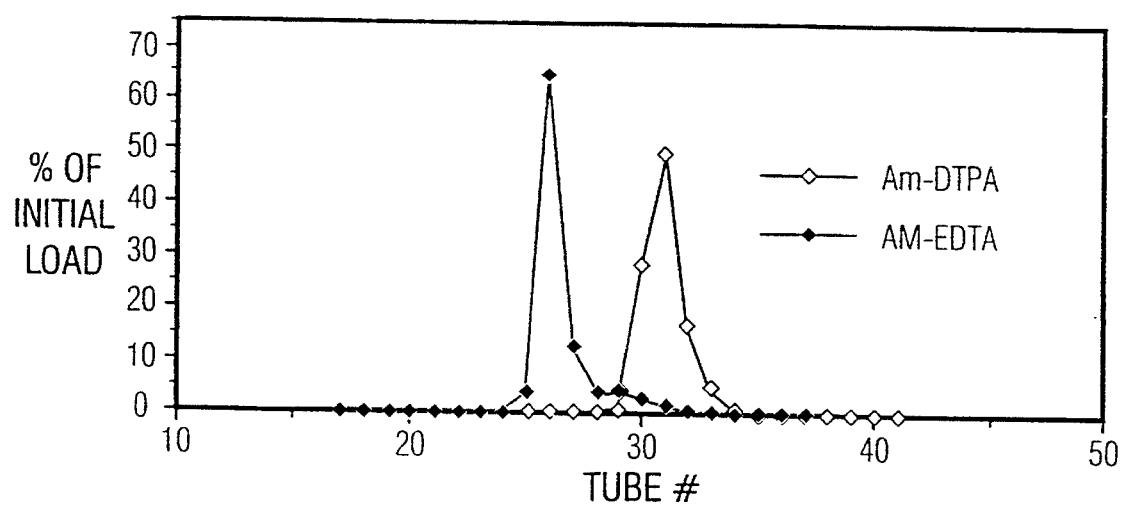
FIG. 1(b) is an elution spectrum of Am-EDTA and Am-DTPA.
Figure 1C:
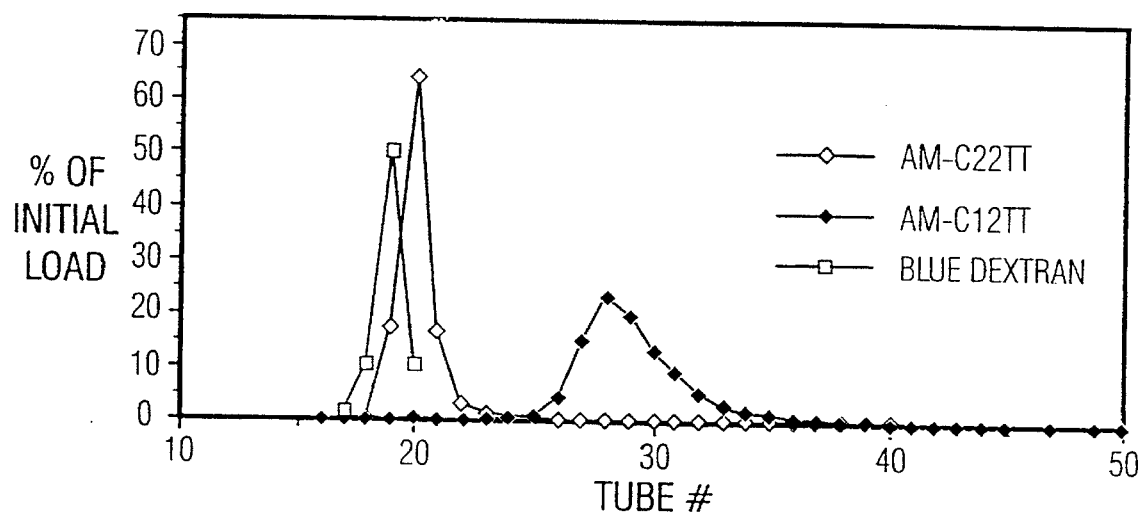
FIG. 1(c) is an elution spectrum of Am-$C_{12}$TT and Am-$C_{22}$TT.

The $^{241}$Am in each of the collected fractions was counted via the 60 keV γ-emission. The resulting elution spectra are shown in FIG. 1 with the amount of $^{241}$Am in individual fractions expressed as percent of the total nuclide loaded. FIG. 1 illustrates elution spectra of $^{241}$Am applied to a column of Sephadex G-15 in three chemical forms. $^{241}$Am-citrate dissociates under the elution conditions, and migration through the gel is inhibited because of hydrolysis. The nuclide can be eluted by subsequent addition of DTPA as shown in FIG. 1(a). $^{241}$Am-EDTA and $^{241}$Am-DTPA form stable chelates which are eluted at their expected relative positions as shown in FIG. 1(b). $^{241}$Am-$C_{12}$TT and $^{241}$Am-$C_{22}$TT also form stable chelates, but increasing micelle formation, especially with $C_{22}$TT, causes partial exclusion from the gel and elution near the void volume as shown in FIG. 1(c).

Elution of $^{241}$Am-citrate was characterized by the relatively low stability of this complex. During the initial phase of the migration, excess citrate was separated from the $^{241}$Am-citrate. The $^{241}$Am-citrate complex dissociated and most of the nuclide hydrolyzed and did not migrate through the resin. Total recovery of $^{241}$Am was only 15%. Addition of a small amount of DTPA to the column followed by elution with buffer increased the recovery to 93%. The elution spectrum of $^{241}$Am was very broad, but the peak appeared essentially at the same position as obtained after gel permeation of $^{241}$Am-DTPA. Both $^{241}$Am-EDTA and $^{241}$Am-DTPA produced sharp peaks separated by 5 fractions. Recoveries were 96% for $^{241}$Am-EDTA and 100.2% for $^{241}$Am-DTPA. The elution of $^{241}$Am-$C_{12}$TT was consistent with the view that a very small fraction of the chelate was present as micelles and this fraction was eluted at the position of the exclusion M.W. The remaining $^{241}$Am-$C_{12}$TT migrated as expected for a true solution. Recovery was >99%. Thus, Am forms a chelate with the alkylated PACA that does not dissociate under the experimental conditions. No value has yet been determined for the thermodynamic stability constants of the new compounds.

The existence of the two chelates is corroborated by the changes observed in the IR spectra as the complexes or chelates are formed. The absorbance maxima near 1600 cm$^{-1}$ and 1400 cm$^{-1}$ of the metal free $C_{22}$TT compound are separated by about 160 cm$^{-1}$, in the Ca chelate by about 190 cm$^{-1}$ and in the Zn-chelate by approximately 220 cm$^{-1}$. At the same time, the corresponding relative peak heights change from 0.895 to 1.664 and 1.761, respectively. The minimum between these two peaks in the uncomplexed form has no special features, but in the Ca-$C_{22}$TT it shows 2 shoulders, and these develop into 2 distinct peaks in the Zn-$C_{22}$TT. The frequency of a minor peak at 880 cm$^{-1}$ (Na-$C_{22}$TT) changes to about 920 cm$^{-1}$ in the chelated form, and the relative peak heights of this to another peak at 720 cm change from 2.357 to 0.772 and 0.905, respectively. Similar shifts of frequencies and relative peak heights have been observed previously for the IR spectra of Na-EDTA vs. alkaline earth EDTA complexes. Although, this is not a proof for the formation of a chelate structure of the metal-$C_{22}$TT, the probability of having a bond analogous to the respective EDTA chelates is given.

Example 9

The ability of Am-citrate and $^{241}$Am-$C_{12}$TT to cross the intestinal mucosa in situ was measured using an intestinal tied-loop technique. Rats were anesthetized and a 18–20 cm segment of the duodenum and proximal jejunum was isolated and rinsed with cold saline. The most proximal portion of this segment was 1 cm distal to the pyloric junction. With the stability of the $^{241}$Am-complex established, known quantities of the corresponding complexes were introduced in vivo directly into the isolated and ligated segment. The animals remained anesthetized to allow for passage of the lipophilic compounds through the intestinal barrier into the body. After 3 hours, the rats were euthanized, the ligated section of the gut was excised and its lumen flushed with saline. Lumen wash, cleaned gut section, combined viscera, liver and the remaining carcass were counted separately. The $^{241}$Am found in the various parts was considered as representative of the distribution of the chelon.

$^{241}$Am given as the citrate was retained almost entirely in the lumen and the gut section. Less than 1% of the total was found in the combined carcass, liver and viscera. Of the $C_{12}$TT only 73% was left in the lumen and gut section, 20% was in the carcass, 3% in the liver and 4% in the viscera. Thus passage of the alkylated compound through the intestinal wall was considerably greater than for $^{241}$Am-citrate.

Example 10

Toxicity studies were performed as indicators of early gross toxicity. It has been found that chelons of similar structure produced hemolysis and some crenation of red cells when incubated with fresh canine blood. Therefore, the crenation hemolysis tests were repeated with the highly purified $C_{12}$-and $C_{22}$-pACAs. Two ml aliquots of fresh canine blood, drawn with a heparinized syringe, were incubated at 37° C. with an equal volume of a 0.1M Tris-buffer containing 10 and 20 mg, respectively, of the Ca chelate of the two compounds whose osmolarity had been adjusted to 270–300 mOsm. After 1 hour and 4 hours of incubation, respectively, blood smears were prepared and examined microscopically and cells were sedimented. No red cell crenation was observed. All sera were slightly pink in appearance but there was no visible difference in color intensity between the two concentrations of the agents.

Example 11

In this Example elimination of Pu by $C_{12}$TT from in vivo tagged canine liver cytosol was observed.

A crude liver homogenate in 0.25M sucrose was obtained from a canine injected with Pu-citrate 7 days before sacrifice. Endogenously bound Pu in this homogenate was bound either to subcellular organelles or high molecular weight proteins and was not ultrafilterable. Centrifugation of this material for 20 min. at 40,000×9 produced a Pu tagged liver cytosol that, mixed 1:1 by weight with glycerol, could be stored at a temperature of $-20°$ C. for extended periods of time. Removing the glycerol by dialysis in 50 mM TRIS, pH 7.5, yielded a medium that was suitable for the in vitro testing of the effectiveness of soluble chelating compounds in the removal of Pu from endogenous ligands.

The frozen cytosol was thawed and dialyzed exhaustively against 50 mM Tris-HCl. Five ml of this material was mixed with 5 ml of a 4 mM solution of the test compound in 0.1M TRIS-HCl adjusted to 270–300 mOsm and pH 7.5. The sample was then incubated at 40° C. for two hours and subsequently filtered under pressure through a molecular filter with a cutoff at 10,000 Daltons. The ratio of the Pu activity in the filtrate to the residue on the filter served as a measure of the chelator effectiveness. Since no clear solution could be obtained from the $C_{22}$TT because of micelle formation, another compound with an 8 carbon alkyl chain ($C_8$TT) was substituted in order to verify the general effectiveness of n-alkyl PACAs in more than a single compound. Filtration of the cytosol carried through the same procedure but without the addition of any of the test compounds served as the control. The following filtrate to residue activities were obtained: Control—0.03, $C_8$TT—0.16 and $C_{12}$TT—0.26. Thus, the alkylated compounds were capable of reacting with endogenously bound Pu.

Example 12

In vivo studies of the compounds of the present invention were performed. The effect of oral treatment on rats given an injection of $^{241}$Am was studied by a) comparing the reduction of an internal burden of $^{241}$Am from rats fed $C_{12}$TT or $C_{22}$TT with the natural biological retention of $^{241}$Am under condition of no chelation treatment; b) examination of histologic sections of tissues obtained from treated rats and c) by comparing the relative weight gain of treated rats and controls during the chelon feeding period. The effect of feeding $C_{12}$TT or $C_{22}$TT on the retention of $^{241}$Am was tested in 3 groups of 9 rats each. Sprague-Dawley rats (Simonson Labs., Gilroy, Calif.), aged 60 days, were used in these studies. The animals were housed in groups of 3 or 4 until treatment was initiated. $^{241}$Am was given via the jugular vein as a single injection in citrate buffer of pH 3.5. One week later, rats were transferred to individual cages and feeding of the chelator was initiated. This delay allowed the nuclide to be incorporated firmly in the target organs, mostly liver and bone.

The first group served as untreated controls, the second and third groups received 50 micro-mole of $C_{12}$TT or $C_{22}$TT/rat or about 200 micro-mole/kg of body weight, respectively, in their daily ration of 25 g of rodent chow. On days 1 and 7 after injection and on days 3, 6 and 10 of chelation treatment, the total body retention of $^{241}$Am was measured using a whole body counter. The animals were necropsied after 10 days of oral chelation therapy and the femora, liver, 1 kidney, viscera and carcass with integument were counted for $^{241}$Am content. The other kidney and a sample of the small and large intestine were prepared for histological evaluation. Whole body retentions as a function of time were evaluated. Terminal organ retentions were measured after necropsy only. The reduction in whole body or organ retention due to oral chelation treatment was expressed as:

$$\text{Reduction} = 1 - \frac{\text{Fractional retention in treated specimen}}{\text{Fractional retention in control specimen}}$$

both taken at the same time after treatment initiation. Results are shown in Table 2 above, which is incorporated into this Example by reference.

Both chelons were highly effective, resulting with $C_{12}$TT in a 29% and $C_{22}$TT in a 44% reduction of the whole body $^{241}$Am. The biggest fractional reduction was seen in the liver burden with 71% and 89%, respectively. However, there also was 20% and 36%, respectively, less in the carcass and 17% and 32% less in the femora indicating that the loss from bone also was accelerated. The insignificance of the loss from the kidney may have been due to the small amount of $^{241}$Am found in this organ. There certainly was no increased retention of $^{241}$Am in the kidneys.

At the age used, rats were growing vigorously. After ten days of oral chelation treatment, there was no statistical difference in weight gain between the three groups. At the end of the feeding period, controls showed a weight gain of 61.1+8.8 g, rats receiving the $C_{12}$-compound gained 55.7+ 11.1 g and those fed the $C_{22}$-compound also showed a gain of 70.2+11.6 9. All animals appeared active and alert.

A segment of the duodenum, the large intestine and kidney were fixed in formalin, embedded in paraffin and histological sections were prepared. The sections were stained with hematoxylin and eosin, and examined microscopically. There was no histological evidence of any tissue toxicity associated with the chelon administration after the ten days of treatment.

Example 13

In this example, animals were injected intravenously with $^{241}$Am-complexed $C_{12}$TT or $K_{11}$TT (K=terminally carboxylated alkyl series) and the rates of elimination from the body were determined. This was determined by whole body counting and counting of the excreta, both urine and feces.

Figure 2:
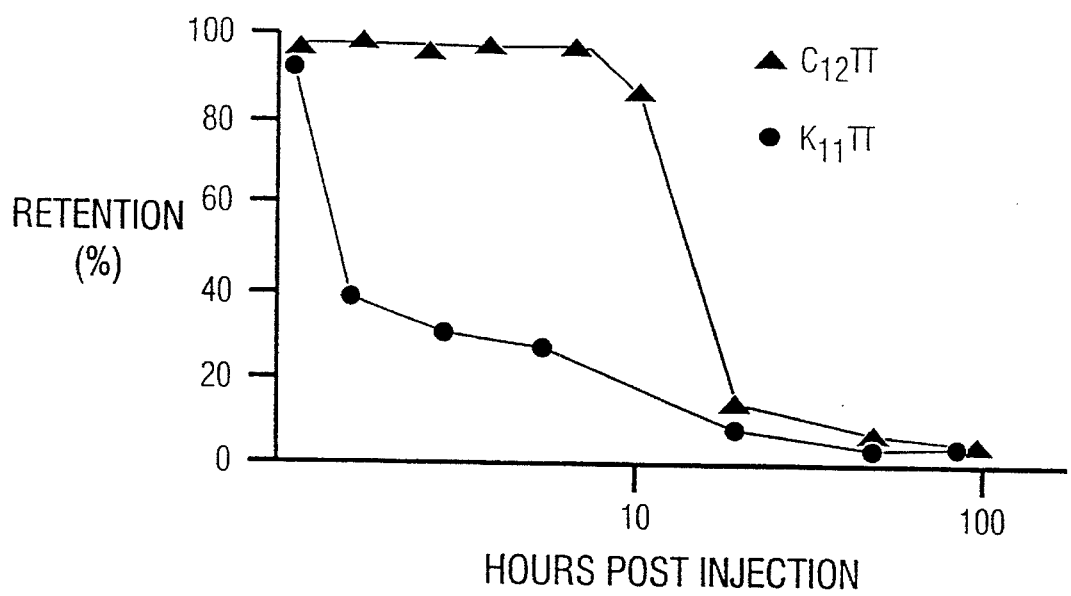
FIG. 2 is a graph illustrating the fraction of body retention of labelled chelating agents as a function of time.

FIG. 2 illustrates the fraction of total body retention of the labeled chelating agents as a function of time after exposure. Complexed $K_{11}TT$ was rapidly eliminated from the body and this was found to be via excretion by the kidney. $C_{12}TT$ was less rapidly excreted but the pathway of excretion was found to be via the liver, through the bile into the feces. This example illustrates that modified polyaminocarboxylic acids have different organ targeting properties and different excretion pathways.

Example 14

In this example the removal by oral administration of $C_{22}TT$ of deposits of previously incorporated $^{239}$plutonium ($^{239}$Pu) from select tissues is demonstrated. Twelve young adult male rats (Sprague-Dawley rats from Simonson Labs, Gilroy, Calif.) were given $^{239}$Pu by intravenous injection. Fourteen days later 6 of the animals were fed $C_{22}TT$ in the diet while the other 6 animals were not fed the compound and served as controls. The delay in beginning the chelation treatment allowed the nuclide to be incorporated firmly in the target organs. After 10 days of feeding, the animals were sacrificed and the Pu content in select tissues was determined by liquid scintillation counting.

As illustrated in Table 5 below, oral administration of $C_{22}TT$ resulted in substantial reductions in Pu content of the liver and the spleen. Modest reductions were also observed in skeletal tissues. Due to the deep burial of Pu in bone deposits, even modest reductions in the skeletal burden are considered pharmacologically important.

TABLE 5

Reduction of $^{239}$Pu organ burden by oral administration of $C_{22}TT$.

| Organ | % Reduction* (untreated) valuesp-value |
|---|---|
| Liver | 71.1 < 0.005 |
| Spleen | 16.9 < 0.01 |
| Femora | 3.5 < 0.375 |
| Lumbar vertebral bodies | 8.4 < 0.375 |

*100 × (1-Pu in treated animals/Pu in untreated, control animals)

Example 15

In this example, dimercaptosuccinic acid (DMSA) is modified by the addition of an alkyl side chain to improve intestinal absorption and tissue penetration for the specific chelation of lead. DMSA is effective for reducing blood levels of Pb, but has limited effectiveness in removing lead burdens from other organs, such as liver, brain and bone. The chemical structure of 2,3-dimercaptosuccinic acid (DMSA) is:

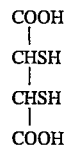

A new, partially lipophilic derivative of DMSA with chelation properties similar to the parent compound has been synthesized. The structure of S-Dodecyl dimercaptosuccinic acid ($C_{12}$DMSA) is:

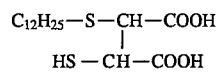

The partial lipophilic character of this molecule has been established in vitro and based on the addition of similar side chains to the polyaminocarboxylic acids (PACA's), it is expected that this compound will be effective orally. The ability of this molecule to bind Pb is demonstrated in vitro (data below). As with the PACA's, the chain length could be changed and other functional groups could be added.

The synthesis of this molecule begins with DMSA and alkylation is carried out under basic conditions, as follows:

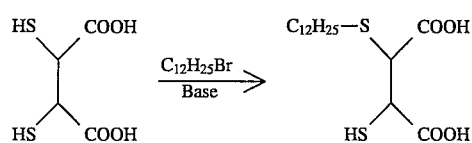

The following 1H-NMR (CDCl$_3$) spectrum was obtained:
Alkyl chain protons—(CH$_2$)$_6$CH$_3$ 0.81–1.67 (m, 30H) Methylene protons bound to oxygen —O—CH$_2$-alkyl 4.15 (t,4H, J=6.7 Hz) Methine protons 3.57 (dd, 2H, J=3.0, J=8.0Hz) Protons of mercapto groups —SH 2.29 (dd, 2H, J=3.0, J=8.0 Hz)

Example 16

In this example, an alkyl side chain is added through a thioether linkage to a dimercaptosuccinic acid diethyl ester (DMS-Et$_2$) molecule. DMS-Et$_2$ is a modification of DMSA already presented in the literature. The example presented here is S-Dodecyl dimercaptosuccinic acid diethyl ester ($C_{12}$DMS Et2). The further modification of the DMS-Et$_2$ molecule improves its pharmacological properties for the penetration of tissues for the chelation of Pb. The structure of S-Dodecyl dimercaptosuccinic acid diethyl ester ($C_{12}$DMS Et2) is:

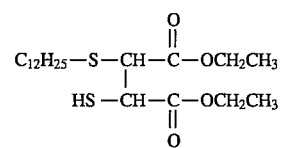

The synthesis of this molecule is:

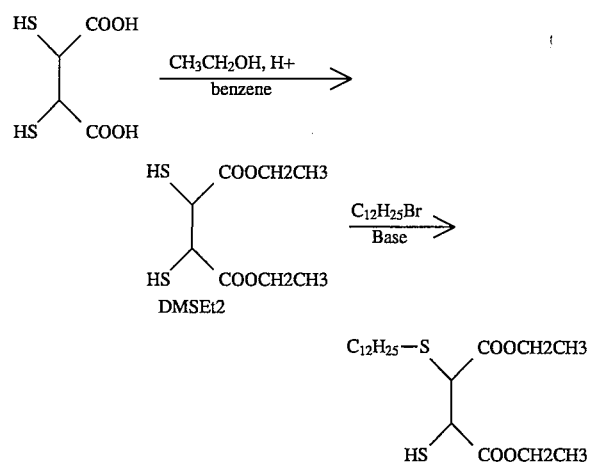

The following 1H-NMR (CDCl$_3$) spectrum was obtained: Alkyl chain protons —(CH$_2$) 11 CH$_3$ 0.81–1.67 (m, 25H) Methylene protons bound to sulfur —S—CH$_2$-alkyl 2.60–2.70 (m 2H) Methine protons —CH—CH—3.66 (t, 1H, J=12 Hz) 3.50 (d, 1H, J=12 Hz) 2.29 (d, 1H, J=12 Hz) Protons of mercapto groups —SH$_{2.29}$ (d, 1H, J=12 Hz) Methylene protons of two ester groups —OCH$_2$CH$_3$ 4.17–4.30 (m, 4H) Methyl protons of two ester groups —OCH$_2$CH$_3$ 1.31 (t, 6H, J=7.0 Hz)

Example 17

The diester analogue of DMSA illustrated below, is modified with longer alkyl side chains (> than 3 carbons) resulting in a molecule with increased lipophilic properties. Ester linkages with greater than 3 carbons are not described in the literature. In this example, the dioctyl ester of DMSA, dimercaptosuccinic acid dioctyl ester [DMS(C$_8$)$_2$] is illustrated. The synthesis of DMS(C$_8$)$_2$ is:

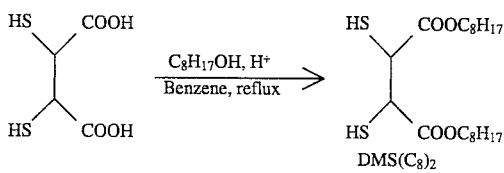

Example 18

In this example, the partial lipophilic character of the modified DMSA molecules and the ability of these new molecules to chelate Pb is demonstrated in vitro. In this example the ability of DMS(C$_8$)$_2$, from Example 17, and C$_2$DMS Et$_2$, from Example 16 to move $^{210}$Pb between lipid and aqueous phases of chloroform and water mixture was measured. This would be an indicator of the ability of the chelator and the chelate-metal complex to penetrate lipophilic barriers. These data would predict that this class of molecules would cross cellular and tissue barriers, including their ability to be given orally.

$^{210}$Pb was dissolved in water. C$_{12}$DMS Et$_2$ and DMS(C$_8$)$_2$ were added and mixed for 10 minutes with chloroform. The solutions were mixed every several hours. The phases separated and the percentage of $^{210}$Pb found in the chloroform phase as a function of time was determined.

TABLE 6

Percentage of aqueous $^{210}$Pb found in chloroform phase as a function of time after adding C$_{12}$DMS Et$_2$ and DMS (C$_8$)$_2$.

| Chelator | Time | |
|---|---|---|
| | 15 min | 16 h |
| C$_{12}$DMS Et$_2$ | 36.5 | 62.2 |
| DMS (C$_8$)$_2$ | 32.2 | 41.9 |

Example 19

In this example, PO$_4^{3-}$ was added to a solution of C$_{22}$TT-Fe. The solubility product of Fe$^{3+}$ and PO$_4^{3-}$ is known to be Ks=21.9. No precipitate was formed indicating the presence of a strong C$_{22}$TT-Fe complex. Reaction with the chelating agent (C$_{22}$TT) reduced the free metal ion concentration to less than the concentration required for precipitation of FePO$_4$ at the given Ks. EDTA-Fe was also reacted as described above with the same result. Thus, the present invention is effective in binding Fe$^{3+}$.

Example 20

In this example, HPO$_4^{-2}$ was added to a solution of C$_{22}$TT-Pb. The solubility product of Pb$^{++}$ and HPO$_4^{-2}$ is known to be Ks=11.4. No precipitate was formed indicating the presence of a strong C$_{22}$TT-Pb complex. Reaction with the chelating agent (C$_{22}$TT) reduced the free metal ion concentration to less than the concentration required for precipitation of PbHPO$_4$ at the given Ks. EDTA-Pb also reacted as above with the same result as C$_{22}$TT. Thus, the present invention is effective in binding Pb$^{++}$.

Example 21

In this example, I$^-$ was slowly added to a solution of C$_{22}$TT-Hg. The solubility product of Hg$^{++}$ and I$^-$ is known to be Ks=28.5. No precipitate was observed, indicating the presence of a strong C$_{22}$TT-Hg complex. Reaction with the chelating agent (C$_{22}$TT) reduced the free metal ion concentration to less than the concentration required for precipitation of HgI$_2$ at the given Ks. EDTA-Hg was also reacted as above with the same result as C$_{22}$TT. Thus, the present invention is effective in binding Hg$^{++}$.

Example 22

In this example, CO$_3^{-2}$ was added to a solution of C$_{22}$TT-Cd. The solubility product of Cd$^{++}$ and CO$_3^{-2}$ is known to be Ks=11.3. No precipitate was observed, indicating the presence of a strong C$_{22}$TT-Cd complex. Reaction with the chelating agent (C$_{22}$TT) reduced the free metal ion concentration to less than the concentration required for precipitation of CdCO$_3$ at the given Ks. EDTA-Cd was also reacted as above with the same result as C$_{22}$TT. Thus, the present invention is effective in binding Cd$^{++}$.

Example 23

In this example, OH$^-$ was added to a solution of C$_{22}$TT-La. The solubility product of La$^{3+}$ and OH$^-$ is known to be Ks=20.3. No precipitate was formed, indicating the presence of a strong C$_{22}$TT-La complex. Reaction with the chelating agent (C$_{22}$TT) reduced the free metal ion concentration to less than the concentration required for precipitation of La(OH)$_3$ at the given Ks. EDTA-La was also reacted as above with the same result as C$_{22}$TT. Thus, the present invention is effective in binding La$^{3+}$.

Example 24

In this example, OH$^-$ was added to a solution of C$_{22}$TT-Ce. The solubility product of Ce$^{3+}$ and OH$^-$ is known to be Ks=21.8. No precipitate was formed, indicating the presence of a strong C$_{22}$TT-Ce complex. Reaction with the chelating agent (C$_{22}$TT) reduced the free metal ion concentration to less than the concentration required for precipitation of Ce(OH)$_3$ at the given Ks. EDTA-Ce was also reacted as above with the same result as C$_{22}$TT. Thus, the present invention is effective in binding Ce$^{3+}$.

Example 25

The metal binding capability of the polyaminocarboxylic acids of the present invention is found to be comparable to that of other known strong chelating agents. An extensive literature review produced the following table:

TABLE 7

Stability constants for different metals (Log K)

| Metal Ion | EDTA | DPTA | COMPOUND 1 | TTHA | COMPOUND 2 | EHPE | HBED | CDTA | EGTA |
|---|---|---|---|---|---|---|---|---|---|
| Mg++ | 8.85 | 9.3 | 7.3 | 9.3 | 9.5 | 8.9 | | 11.1 | 5.3 |
| Ca++ | 10.6 | 10.8 | 9.6 | 9.9 | 9.4 | | | | |
| Sr++ | 8.3 | 9.6 | 8.4 | 9.3 | 6.7 | | | 10.6 | 8.4 |
| Hg++ | 21.6 | 26.4 | 24.7 | 26.1 | 27.7 | | | 24.8 | 22.9 |
| Pb++ | 17.8 | 18.7 | | 18.5 | | | 18.2 | 20.2 | 14.5 |
| Cd++ | 16.4 | 19 | 17.4 | 18.6 | 17.8 | | 10.5 | 19.8 | 16.1 |
| Cu++ | 18.7 | 21.4 | | 20.5 | | 8 | 21.4 | 21.9 | 17.6 |
| Zn++ | 16.4 | 18.7 | | 18 | | 16.8 | 18.4 | 19.4 | 12.6 |
| Co++ | 16.3 | 19.7 | | 18.4 | | | 19.9 | 19.6 | 12.4 |
| Mn++ | 13.8 | 15.5 | | 16 | | 8.9 | 14.8 | 17.4 | 12.2 |
| Ni++ | 18.5 | 20.2 | | 19.4 | | 19.6 | 19.3 | 20.2 | 13.5 |
| Fe+++ | 25 | 28 | | 26.8 | | 33.9 | 39.7 | 30 | 20.5 |
| Mn+++ | 25.3 | 31.1 | | | | | | 28.9 | 22.7 |
| Cr+++ | 23.4 | | | | | | | | |
| Ce+++ | 15.9 | 22.3 | | | | 13.1 | 17.5 | 17.5 | 16.1 |
| La+++ | 15.5 | 19.5 | | 22.3 | | | | 17 | 15.5 |
| Y+++ | 18.1 | 22.3 | | | | | | 19.9 | 17.2 |
| Th+++ | 35.3 | 48 | | | | | | 38.3 | |
| Th++++ | | 28.8 | | 31.9 | | | | 25.6 | 7.3 |
| Zr++++ | 29.4 | 36.9 | | 19.7 | | | | | |

Compound 1 and 2, respectively, had been monoalkylated in position $N_2$ (compound 1) and dialkylated in positions $N_2$ and $N_3$ (compound 2) Ref. Schwarzenbach et al; Helvetica Chem. Acta, XL, VI, 199. pp 1886–1092.

The modified PACA's of the present invention retain the basic structural and functional properties of PACA's. Thus their affinity for metals would not be expected to be substantially different from basic PACA's that have similar or related structures.

EDTA, DTPA, and TTHA are well established strong chelators for a variety of heavy metals. If a single alkyl group replaces a carboxymethyl group of DTPA (Compound 1, Table 7), the stability constant, compared with the parent DTPA, does not change substantially. The resulting stability constants with some heavy metals are intermediate between those of the Me-EDTA and Me-DTPA complexes. As an example, the $Hg^{++}$ chelate of Compound 1 (pK=24.7) has a stability between Hg-DTPA (pK=26.4) and Hg-EDTA (pK=21.6); or for the Cd-chelates, its value (pK=17.4) is between Cd-DTPA (pK=19.0) and Cd-EDTA (pK=16.4). Compound 1 is similar to the compounds of the present invention, e.g. $C_{22}TT$, in which one carboxymethyl group is replaced with a long chain alkyl group. Results show that the replacement of one carboxymethyl does not substantially alter the stability constant for heavy metals.

Example 26

Increased excretion of lead (Pb) with oral administration of 1-N-Dodecyl-diethylenetriamine tetraacetic acid ($C_{12}DT$) and 1-N-Dodecyl-triethylenetetramine pentaacetic acid ($C_{12}TT$) was observed. In this example nine mature male rats were given 0.5 $\mu$Ci$^{210}$Pb by injection into the jugular vein. After 7 days, the rats were randomly divided into groups of 3 and started on one of the following treatments: 1) Placebo; 2) 50 $\mu$Mole/d of $C_{12}DT$; 3) 50 $\mu$Mole/d of $C_{12}TT$. The chelators were added to the daily food ration and fed for 10 additional days. The delay in beginning the chelation treatment allowed the lead to be incorporated into the target organs. Most of the lead will deposit in the skeletal system and usually be buried, or somewhat locked in as new bone is deposited on top of the lead deposits. Thus even very small reductions in skeletal concentrations of lead are considered pharmacologically important. At the end of 10 days, both femurs were removed and the remainder of the carcass (without the viscera) were counted for total Pb activity by gamma spectroscopy. At the end of 10 days of treatment there were decreases in the amount of $^{210}$Pb in the $C_{12}DT$ and $C_{12}TT$ treated animals compared with controls in both the femurs and the residual carcass that included all of the remainder of the skeletal tissues (Table 8).

TABLE 8

Amount of $^{210}$Pb ($\mu$Ci ± standard error of the mean) following oral administration of $C_{12}DT$ and $C_{12}TT$.

| Organ | Control | $C_{12}DT$ | $C_{12}TT$ |
|---|---|---|---|
| Carcass | 0.194 ± 0.003 | 0.168 ± 0.014 | 0.184 ± 0.004 |
| Both Femora | 0.022 ± 0.001 | 0.018 ± 0.002 | 0.019 ± 0.001 |

Example 27

Increased excretion of lead following the oral administration of $C_{22}TT$ was observed. In this example, 2 adult male rats were given 0.5 $\mu$Ci of $^{210}$Pb by injection into the jugular vein. One week later the animals were whole body counted to provide a baseline value and chelation treatment was started. $C_{22}TT$ was added to the daily food ration at a dose of 50 $\mu$M/day. The animals were periodically whole body counted during the experiment which lasted for another 2 weeks. After 7 days, the control, untreated animal retained 69.6% of the $^{210}$Pb while the treated animal retained 64.0%. One week later, at the end of the experiment, the treated animal retained 62.8% of the initial Pb while the control animal retained a greater amount, 67.9%. These data suggest that $C_{22}TT$ treatment was effective in reducing the total body amount of Pb when given soon after exposure to Pb.

Example 28

Increased excretion of iron following the oral administration of $C_{22}TT$ was observed. In this example, a male rat was injected with $^{59}$Fe and 3 days later the red blood cells were collected and washed. The allowed time for the $^{59}$Fe to become incorporated into heme (hemoglobin) iron pool. The presence of radioactive iron in the red blood cells was confirmed by gamma spectroscopy. The cells were heat damaged (55° C. for 20 minutes) and equal portions were injected intraperitoneally into 2 male rats. Three days later each rat was whole body counted and the amount of $^{59}$Fe retained was determined. One animal was allowed to eat a diet to which 50 μM $C_{22}TT$ was added to the daily food ration and the other animal served as an untreated control. After 3 weeks on chelation treatment the control rat retained 86.2% of the initial amount of $^{59}$Fe while the $C_{22}TT$ treated rat retained 82.6% of the initial amount. These results indicate that $C_{22}TT$ can reduce the total body amount of Fe that was previously incorporated into Fe-containing molecules.

Example 29

Decreased liver iron following the oral administration of $C_{22}TT$ was observed. In this example, rats were fed an iron deficient diet for 1 week before chelation treatment was started. One rat was given 50 μM of $C_{22}TT$ added to the daily food ration while another rat was given an intraperitoneal injection of 25 mg desferrioxamine (DFO) every other day. Two rats were given no chelation treatment and served as controls. The animals were housed in metabolic cages and urine was collected. After 1 week of treatment, the livers were perfused with saline to remove excess blood and iron content determined by atomic absorption. The amount of iron in liver from the $C_{22}TT$ treated rat was 78% of the controls while liver from the DFO treated rat contained about 105% of the control. There was a 14% increase in Fe content in the urine from the DFO treated rat, but unchanged in the $C_{22}TT$ treated rat. These results confirm that DFO (an established Fe chelator) increased the urinary excretion of iron, as expected, but the $C_{22}TT$ caused a greater reduction in the liver content of iron.

Summary

Accordingly, it will be appreciated that the present invention provides methods and compositions for treating metal poisoning in warm blooded mammals, such as humans, and contamination which overcomes many of the limitations of the conventional art. Specifically, the present invention provides compositions which are partially lipophilic and, therefore, are capable of easy and effective oral administration. This is a significant advancement over conventional chelation therapy which is administered intravenously.

The present invention also teaches methods and compositions for targeting specific heavy metals and specific tissues. In this regard synthesis techniques and selection parameters are disclosed for synthesis of compositions which can accomplish targeting of specific metals in specific organs. This is a significant advancement over conventional methods which are unable to target specific tissues, and in fact are effective mainly in removing metals from blood.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for removing a metal from the tissues of a warm blooded mammal suffering metal poisoning, comprising the steps of:
   a) obtaining a partially lipophilic chelating agent which is capable of being absorbed across the intestine of the mammal, said chelating agent being capable of forming a complex with the heavy metal at physiological pH, said chelating agent comprising a polyaminocarboxylic acid having the following formula:

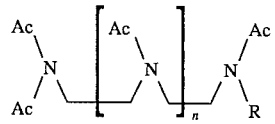

wherein Ac is $CH_2COOH$, R is an alkyl substituent, or alkyl derivative, having from 6 to to 22 carbon atoms, and n is an integer from 1 to 3; and b) orally administering the chelating agent to complex with said metal in the mammal, wherein said metal is from Group II-A, III-B, IV-B, V-B, VI-B, VII-B, VIII, I-B, II-B, III-A or IV-A of the periodic table (CAS Version) and;

c) eliminating said complex from the mammal by excretion.

2. A method for removing a metal from the tissues of a mammal suffering metal poisoning as defined in claim 1 wherein the chelating agent comprises a potyaminocarboxylic acid synthesized from triethylenetetramine.

3. A method for removing a metal from the tissues of a mammal suffering metal poisoning as defined in claim 1 wherein the chelating agent comprises a polyaminocarboxylic acid synthesized from diethylenetriamine.

4. A method for removing a metal from the tissues of a mammal suffering metal poisoning as defined in claim 1 wherein the tissue is liver.

5. A method for removing a metal from the tissues of a mammal suffering metal poisoning as defined in claim 1 wherein the polyaminocarboxylic acid chelating agent further comprises a phosphoric acid group bound to the alkyl substituent.

6. A method for removing a metal from the tissues of a mammal suffering metal poisoning as defined in claim 1 wherein the polyaminocarboxylic acid chelating agent further comprises an alcohol group bound to the alkyl substituent.

7. A method for removing a metal from the tissues of a mammal suffering metal poisoning as defined in claim 1 wherein the tissue is skeletal tissue.

8. A method for removing a metal from the tissues of a mammal suffering metal poisoning as defined in claim 7 wherein the polyaminocarboxylic acid chelating agent further comprises a sugar group bound to the alkyl substituent.

9. A method for removing a metal from the tissues of a mammal suffering metal poisoning as defined in claim 7 wherein the polyaminocarboxylic acid chelating agent further comprises a phosphonate group bound to the alkyl substituent.

10. A method for removing a metal from the tissues of a mammal suffering metal poisoning as defined in claim 1 wherein the chelating agent is capable of forming a complex with the heavy metal at the normal physiological pH of the mammal.

11. A method for removing a metal from the tissues of a mammal suffering metal poisoning as defined in claim 1 wherein the chelating agent has a greater affinity for the heavy metal than for calcium or zinc in the mammal.

12. A method for removing a metal from the tissues of a mammal suffering metal poisoning as defined in claim 1 wherein the heavy metal is lead.

13. A method for removing a metal from the tissues of a mammal suffering metal poisoning as defined in claim 1 wherein said mammal is a human.

14. A method for treating metal poisoning in a mammal comprising the steps of:
   a) obtaining a partially lipophilic chelating agent which is capable of being orally administered to the mammal and which is capable of passing into tissue cells containing the heavy metal, which chelating agent is capable of forming a complex with the heavy metal at physiological pH and which has a greater affinity for the heavy metal than for physiologic calcium or zinc, and wherein said metal is from Group II-A, III-B, IV-B, V-B, VI-B, VII-B, VIII, I-B, II-B, III-A or IV-A of the periodic table (CAS Version), wherein said chelating agent comprises a polyaminocarboxylic acid containing an alkyl substituent group having from 6 to 22 carbon atoms; and
   b) orally administering the chelating agent to the mammal.

15. A method for treating metal poisoning in a mammal as defined in claim 14 wherein the complex formed between the heavy metal and the chelating agent is less toxic than the heavy metal alone.

16. A method for treating metal poisoning in a mammal as defined in claim 14 wherein the chelating agent is selected such that the complex formed by the chelating agent and the heavy metal is eliminated by the mammal.

17. A method for treating metal poisoning in a mammal as defined in claim 14 wherein the chelating agent comprises a carboxylate group bound to the alkyl substituent.

18. A method for treating metal poisoning in a mammal as defined in claim 14 wherein the chelating agent comprises an alcohol group bound to the alkyl substituent.

19. A method for treating metal poisoning in a mammal as defined in claim 14 wherein the chelating agent further comprises a sugar moiety bound to the alkyl substituent.

20. A method for treating metal poisoning in a mammal as defined in claim 14 wherein the chelating agent comprises a carboxylate group bound to the alkyl substituent.

21. A method for treating metal poisoning in a mammal as defined in claim 14 wherein the chelating agent has the following general formula:

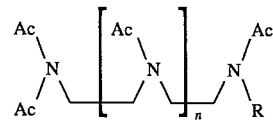

wherein Ac is $CH_2COOH$, R is the alkyl substituent, or alkyl derivative, having from 6 to 22 carbon atoms, and n is an integer from 1 to 3.

22. A method for treating metal poisoning in a mammal as defined in claim 14 wherein the metal is lead.

23. A method for treating metal poisoning in a mammal as defined in claim 14 wherein the metal is iron.

* * * * *